United States Patent
Kim et al.

(10) Patent No.: US 8,012,468 B2
(45) Date of Patent: Sep. 6, 2011

(54) DENDRITE CELLS TRANSDUCED WITH RECOMBINANT ADENOVIRUS ADVCEA WHICH GENERATE CEA-SPECIFIC CYTOTOXIC T LYMPHOCYTES, VACCINE AND PHARMACEUTICAL COMPOSITION COMPRISING THE SAME

(75) Inventors: Tai-gyu Kim, Seoul (KR); Hyun-il Cho, Seoul (KR); Hye-jin Kim, Seoul (KR); Seoug-taek Oh, Seoul (KR)

(73) Assignee: Catholic Universtiy Industry Academic Cooperation Foundation (KR)

( * ) Notice: Subject to any disclaimer, the term of this patent is extended or adjusted under 35 U.S.C. 154(b) by 1053 days.

(21) Appl. No.: 11/570,282

(22) PCT Filed: Jun. 11, 2004

(86) PCT No.: PCT/KR2004/001400
§ 371 (c)(1), (2), (4) Date: Feb. 23, 2007

(87) PCT Pub. No.: WO2005/120566
PCT Pub. Date: Dec. 22, 2005

(65) Prior Publication Data
US 2007/0243197 A1    Oct. 18, 2007

(51) Int. Cl.
*C12N 5/00* (2006.01)
*A01N 63/00* (2006.01)
(52) U.S. Cl. ..................... 424/93.21; 435/325
(58) Field of Classification Search ............... 435/320.1, 435/325; 424/93.1
See application file for complete search history.

(56) References Cited

U.S. PATENT DOCUMENTS
6,548,068 B1 * 4/2003 Schlom et al. ............. 424/199.1

OTHER PUBLICATIONS 3 pages of search reports from kctc.kribb.re.kr.*
Cho et al., 2003, Vaccine, vol. 22, pp. 224-236.*
Hammarstrom S., 1999, Cancer Biol., vol. 9, pp. 67-81.*
Finn et al., 2002, Current Opinion in Immunology, vol. 14, pp. 172-177.*
Robbins et al., 1991, Cancer Res., vol. 51, vol. 3657-3662.*
Tsang et al., 2001, Cancer Res., vol. 61, pp. 7568-7576.*
Hyun-Il Cho et al., "In vitro induction of carcinoembryonic (CEA)-specific cytotoxic T lymphocytes by dendritic cells transduced with recombinant adenoviruses," Vaccine, vol. 22, pp. 224-236, Dec. 12, 2003.
J. Qiao et al., "Tumor-specific transcriptional targeting of suicide gene therapy," Gene Therapy, vol. 9, pp. 168-175, Feb. 2002.
Hiroyuki Goto et al., "Gene Therapy Utilizing the Cre/loxP System Selectively Suppresses Tumor Growth of Disseminated Carcinoembryonic Antigen-Producing Cancer Cells," Int. J. Cancer, vol. 94, pp. 414-419, 2001.
Masato Ueno et al., "Tumor-specific Chemo-radio-gene Therapy for Colorectal Cancer Cells Using Adenovirus Vector Expressing the Cytosine Deaminase Gene," Anticancer Research, vol. 21, pp. 2601-2608, 2001.

* cited by examiner

*Primary Examiner* — Peter Paras, Jr.
*Assistant Examiner* — David A Montanari
(74) *Attorney, Agent, or Firm* — Kenneth H. Sonnenfeld; King & Spalding LLP

(57) ABSTRACT

The present invention relates to an antitumor immune response, and in more detail, to a method for inducing cytotoxic T lymphocytes specific to a tumor-associated antigen that acts specifically on tumor cells.

Immunotherapy using the present invention may be most effective among immune therapies that use immunity of our body, because in the present invention, CEA-specific cytotoxic T lymphocytes can be induced in vitro by using a dendritic cell transduced with a recombinant adenovirus.

Further, immunotherapy using the present invention can function as a powerful tool for tumor prevention or treatment, if being used in combination with antitumor vaccines or other treatments.

8 Claims, 8 Drawing Sheets

SEQUENCE LISTING

```
<160> NUMBER OF SEQ ID NOS: 4

<210> SEQ ID NO 1
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
```

-continued

```
cgaagctagc atggagtctc cctcggcccc                                      30

<210> SEQ ID NO 2
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gcgcgctagc ctatatcaga gcaaccccaa cc                                   32

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Tyr Leu Ser Gly Ala Asn Leu Asn Leu
1               5

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Thr Tyr Ala Cys Phe Val Ser Asn Leu
1               5
```

DENDRITE CELLS TRANSDUCED WITH RECOMBINANT ADENOVIRUS ADVCEA WHICH GENERATE CEA-SPECIFIC CYTOTOXIC T LYMPHOCYTES, VACCINE AND PHARMACEUTICAL COMPOSITION COMPRISING THE SAME

TECHNICAL FIELD

The present invention relates to an antitumor immune response, and in more detail, to a method for inducing cytotoxic T lymphocytes specific to a tumor-associated antigen that acts specifically on tumor cells.

BACKGROUND OF THE INVENTION

In current cancer treatments, after many cancer tissues as possible are surgically removed, the remaining cancer cells are killed by radiotherapy and chemotherapy. This is currently the main method to treat tumors. But surgery has several problems, such as the removal range is broad and there is a recurrent risk by micrometastasis. Radiotherapy and chemotherapy also have many side effects. Especially, in the case of anti-tumor drugs, they are not always effective in all types of cancer. In many cases, remaining cancer cells that were exposed to an anticancer drug have a resistance to it, keep on growing and even metastasize to other organs. In the result, the cancer is impossible to fully treat.

Accordingly, there is a limit to overcome cancer using only these therapies. Therefore, immunotherapy is now being looked at as a new cancer treatment, which uses the immunity of our body.

Immunotherapy has side effects, but they are less severe than other treatments and is more effective in being used in combination with other treatments. Thus is the importance of immunotherapy. Immunotherapy is an indirect treatment that treats cancer by activating a patient's immune response whereas surgery, chemotherapy and radiotherapy directly attack cancer cells.

Broadly, the different types of immune responses fall into two categories: a humoral immune response and a cell-mediated immune response. The humoral immune systems function to make antibodies for degradation and removal of antigens, e.g. infectious microbes, viruses and bacteria, invading the human body. Meanwhile, the cellular immune response relates to immune surveillance mechanisms and produces cells (lymphocytes) specific to any antigen (cancer cell). The cellular immune response is more important than the humoral immune system in tumor-related immunity. Like this, antitumor immune response is generally related to cell-mediated responses; therefore it is known that the role of CD8+ cytotoxic T lymphocyte is important for this reaction. Nowadays, a tumor-associated antigen (TAA) has been studied to induce antitumor T cell. Also, the researches for T cell immunotherapy against tumor have been continued according to development of recombinant DNA technology.

As one of these attempts, U.S. Pat. No. 5,698,530 disclosed "a recombinant virus comprising a vaccinia virus into which a carcinoembryonic antigen (CEA) gene is inserted which recombinant virus expresses CEA on the surface of cells infected therewith and which recombinant virus elicits a cell medicated immune response in vivo directed against CEA and cells expressing CEA".

However, in case that the antitumor immune response is induced by recombinant virus in vivo and then it is adopted for treatment of patients suffered from cancers, there is a limit that it is insufficient to supplement weakened immunity of the patients. Therefore, there has been a requirement toward a development of more effective immunotherapy and especially, the method for inducing cytotoxic T lymphocytes in vitro.

DETAILED DESCRIPTION OF THE INVENTION

The object of the present invention to solve the above problem is to provide a method for in vitro induction of antigen-specific cytotoxic T lymphocytes that have a specific act on tumor cells.

To accomplish the object, the present invention provides a recombinant adenovirus expressing CEA, AdVCEA and a dendritic cell transduced with a recombinant adenovirus, AdVCEA, which generates CEA-specific cytotoxic T lymphocytes, wherein the dendritic cell generates CEA-specific cytotoxic T lymphocytes in vitro.

The present invention provides not only an antitumor vaccine and a pharmaceutical composition for treating tumor comprising the dendritic cell, but also an antitumor vaccine and a pharmaceutical composition for treating tumors comprising CEA-specific cytotoxic T lymphocytes generated by the dendritic cell. Furthermore, the present invention provides a method for inducing CEA-specific cytotoxic T lymphocytes in vitro using a dendritic cell transduced with a recombinant adenovirus, AdVCEA.

The present invention is described in detail below.

First, the present invention provides a dendritic cell transduced with a recombinant adenovirus, AdVCEA generating CEA-specific cytotoxic T lymphocytes in vitro and a method for inducing CEA-specific cytotoxic T lymphocytes in vitro using a dendritic cell transduced with the recombinant adenovirus, AdVCEA.

Among immunotherapies for treating tumor, the present invention is based on immunotherapy of identifying peptide epitope originated from a tumor antigen and then treating the tumor by using cytotoxic T cells specific to the tumor antigen. To induce cytotoxic T cells specific to tumor cells, an adequate tumor-related antigen (TAA) should be selected. A tumor-related antigen may be prostate-specific antigen, HER-2/neu, MUC-1, point mutated or wild-type overexpressed p53, MAGE antigen and CEA (carcinoembryonic antigen) and so on.

In the present invention, CEA is used as a tumor-related antigen, and it is an oncofetal glycoprotein of 180 kDa and a soluble tumor marker. CEA is expressed over 95% in colorectal, gastric and pancreatic carcinomas, in approximately 50% of breast cancer, and in 70% of non-small cell lung cancers so that it may be a powerful target TAA for tumor immunotherapy. As described above, CEA is used as TAA in the present invention and therefore, dendritic cells (DCs) according to the present invention can generate CEA-specific cytotoxic T lymphocytes that have an effect on several kinds of tumors.

Since antigen presentation by the tumor cells themselves appears insufficient to induce an adequate immune response, professional antigen-presenting cells (APCs) are required. In the present invention, DCs are used as antigen-presenting cells because DCs may function as potent antigen-presenting cells for antigen presenting pathway to MHC class I molecules which essential to induce antigen-specific cytotoxic T lymphocytes. DCs, a kind of antigen-presenting cells used for induction of antigen-specific cytotoxic T lymphocytes, are originated from bone marrow and are present as immature form in peripheral site. And then DCs are known to initiate or regulate the immune response of T lymphocytes with activity to antigens by recognizing the antigens and stimulating proliferation-suppressed T lymphocytes. Also, DCs may be preferable as antigen-presenting cells used for induction of antitumor immune response because they express MHC, CD80, CD86, LFA (lymphocyte function-associated antigen) 1 and 3, ICAM (intracellular adhesion molecule) 1 and 3, and so on in high level, besides cytotoxic T lymphocytes. Furthermore, DCs have advantages in that they are easily transduced by recombinant adenovirus (AdV) and are capable of transporting antigens from the endocytic compartment to the cytosol, leading to cross-presentation on HLA class I molecules to CD8+ T-cells even in the absence of de novo synthesis.

As methods for transporting genetic material to DCs, there are techniques such as electroporation, lipid-mediated transfection, calcium phosphate precipitation and virally-mediated gene transfer, but the present invention especially use a viral vector to express tumor antigens by transferring tumor genes to DCs. Among viral vectors, a recombinant adenovirus is preferable because it has advantages that it can be inserted with large size of extracellular antigen gene, and infects target cells not to do cell division and then express antigen proteins.

A recombinant adenovirus expressing CEA according to the present invention was constructed by inserting CEA synthesized from LoVo cell line into the Adeno-X™ AdVCEA constructed as described above was transfected to host cell, HEK 293 cell line, and cultured to high titer of viral stock.

Transduction of dendritic cell by the recombinant adenovirus, AdVCEA (Accession Number: KCTC 10649BP) is preferably performed at MOI of 100~2,000, and more preferably, at MOI of 500~1,000. The range of MOI was determined by considering transduction efficiency and toxicity of the virus itself or concern with the antigen influx and so on, because the efficiency of transduction is very low in case below MOI 100 and adenoviruses may express toxicity to target cells in case above MOI 2,000. The safety test of using adenovirus in the present invention was performed through detecting apoptosis of target cells, as described in the following example.

DCs transduced with recombinant adenoviruses were incubated in the medium containing both GM-CSF and IL-4, and matured in the presence of TNF-α and $PEG_2$. Subsequently, cytotoxic T lymphocytes specific to CEA were induced in vitro by pulsing the DCs with CEA peptide and so on in HLA-A2-positive T2 cell line from healthy donors. Whether cytotoxic T lymphocytes were generated or not, was detected by proliferation assay. Further, cytolytic activity of the cytotoxic T lymphocytes was determined by chromium release assay. In addition, tumor preventive and treating activity was revealed to be excellent in case of AdVCEA/DC according to the present invention when the activities were tested using animal models.

The present invention provides not only an antitumor vaccine and a pharmaceutical composition for treating tumor comprising the dendritic cell, but also an antitumor vaccine and a pharmaceutical composition for treating tumor comprising CEA-specific cytotoxic T lymphocytes generated by the dendritic cell. They can function as an antitumor vaccine or a pharmaceutical composition for treating tumor, which works against several kinds of tumor, not limited to a kind of tumor, since the antitumor vaccine and the pharmaceutical composition for treating tumor according to the present invention comprise DCs which generate CEA-specific cytotoxic T lymphocytes or the CEA-specific cytotoxic T lymphocytes generated by the DCs.

BEST MODE FOR CARRYING OUT THE INVENTION

Figure 1:
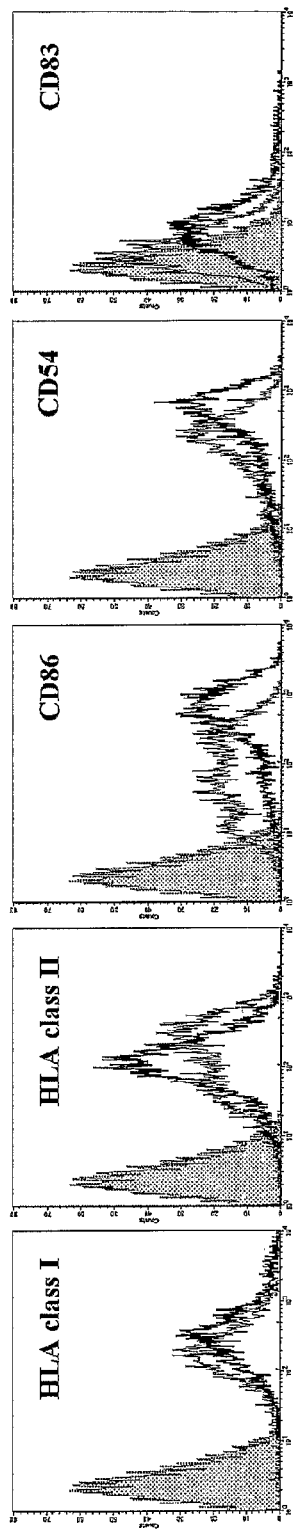
FIG. 1 shows transduction efficiency of adenovirus vector at various multiplicities of infection (MOI) and FIG. 2 shows surface marker expression of adenovirus-infected DCs.

The present invention is described in more detail in the following examples, but it should be understood that the examples are intended to illustrate the present invention, but not limit the invention.

Cell Lines and Method of Cultivation

All cell lines and the methods of cultivation used in following examples are as below.

Colorectal carcinoma cell lines SW403 (human leukocyte antigen (HLA)-A2, A3), SW480 (HLA-A2), LoVo (HLA-A11) were purchased from the American Type Culture Collection (ATCC; Rockville, Md., USA). All of the cell lines were cultured in Dulbecco's modified Eagle medium (DMEM; GibcoBRL, Grand Island, N.Y., USA) supplemented with 15% fetal bovine serum (FBS), 2 mM L-glutamine, 100 U/ml penicillin, and 100 μg/ml streptomycin (GibcoBRL). The HLA-A2-positive T2 cell line was also purchased from ATCC, and maintained with Iscove's modified Dulbecco's medium (IMDM; GibcoBRL) containing 20% FBS. The human adenovirus 5-transformed human embryonic kidney 293(HEK 293; ATCC, CRL1573) cell line and anti-CEA monoclonal antibody (MAb) producing hybridoma cell line T84.66A3.1A.1F2 (ATCC, HB8747) was maintained in DMEM with 10% FBS. Epstein-Barr virus (EBV)-transformed B lymphoblastoid cell lines (LCL) were established from donor PBMCs by EBV transformation and maintained in RPMI-1640 (GibcoBRL) with 10% FBS.

Peptides and Peptide Loading

Peptides and the methods of peptide loading used in following examples are as below.

The CEA peptides, CAP-1 (HLA-A2-restricted, YLS-GANLNL (SEQ ID NO: 3)) and CEA652 (HLA-A24-restricted, TYACFVSNL (SEQ ID NO: 4)) were purchased from AnyGen Co. Ltd. (Kwangju, South Korea). The peptides were dissolved in dimethylsulfoxide (DMSO; Sigma) at a concentration of 10 mg/ml and stored at −70° C. Matured DCs, cultured for an additional 2 days in the presence of TNF-α and $PEG_2$, were used for the proliferative assay. For peptide stripping, DCs or target cells were washed once in cold 1% bovine serum albumin (BSA)/PBS solution, and re-suspended at $5×10^6$ cells/ml in stripping buffer [0.13M L-ascorbic acid, 0.06M sodium phosphate monobasic (pH 3.0), 1% BSA, 3 µg/ml of $β_2$-microglobulin (Sigma), 10 µg/ml of peptide]. After incubation for 2 min on ice, the cells were neutralized with cold neutralizing buffer [0.15M sodium phosphate monobasic (pH7.5), 1% BSA, 3 µg/ml of $β_2$-microglobulin, 10 µg/ml of peptide]. Subsequently, the cells were re-suspended in peptide solution [PBS, 1% BSA, 20 µg/ml of DNase (Sigma), 3 µg/ml of $β_2$-microglobulin, 20 µg/ml of peptide], and incubated for 2 h at room temperature.

Example 1

Construction of Recombinant Adenovirus

The recombinant AdV vector encoding CEA was constructed using the Adeno-X™ Expression System (Clontech, Palo Alto, Calif., USA), according to the manufacturer's instructions. First, RNA was extracted from LoVo cell line expressing CEA protein and then cDNA was synthesized therefrom using Reverse Transcriptase AMV kit (Roche Molecular Biochemicals). The CEA cDNA was amplified by a reverse transcriptase-polymerase chain reaction (RT-PCR) using CEA sense primer 5'-CGAAGCTAGCATG-GAGTCTCCCTCGGCCCC-3' (SEQ ID NO: 1) containing the NheI site, and CEA antisense primer 5'-GCGCGCTAGC-CTATATCAGAGCAACCCCAACC-3' (SEQ ID NO: 2) containing the NheI site. The PCR products obtained were cloned in shuttle vector at the NheI site, and sequenced to identify possible Taq polymerase errors. Subsequently, the CEA expression cassette was inserted into Adeno-X™ viral DNA. After packaging the recombinant adenoviral DNA into infectious AdV by transfecting HEK 293 cells, the adenovirus containing CEA gene (AdVCEA) was amplified and purified from cell lysates by banding twice in CsCI density gradients. Viral products were desalted and stored at −80° C. in phosphate-buffered saline (PBS) containing 10% glycerol (v/v). A similar protocol was used to generate recombinant AdV encoding green fluorescent protein (AdVGFP). The titer of the viral stock determined by using the tissue culture infectious dose ($TCID_{50}$) method was $1×10^9$/ml.

Example 2

Transduction of DCs and Analysis of CEA Expression

Generation and Culture of DCs

DCs were generated using the procedure described by Romani et al. Briefly, the mononuclear cells of healthy volunteers, isolated by Ficoll-Hypaque density gradient, were plated at $10^7$ cells per well in six-well plates and allowed to adhere for 2 h. Non-adherent cells were removed and adherent cells were cultured for 7 days in a RPMI-1640 complete medium containing 100 ng/ml of granulocyte-macrophage colony-stimulating factor (GM-CSF; Endogen, Woburn, Mass., USA) and 500 U/ml of interleukin-4 (IL-4; Genzyme, Cambridge, Mass., USA). To induce the CEA-specific T-cell lines, the monocyte-derived DCs were cultured for an additional 2 days in the presence of 200 U/ml of tumor necrosis factor-α (TNF-α; Endogen) and 1 µg/ml of prostaglandin $E_2$ ($PEG_2$; Sigma, St. Louis, Mo., USA) to induce final maturation.

Transduction Efficiency and Determination of Cea Expression Level (1) Flow Cytometry For determining transduction efficiency, $5×10^5$ DCs were suspended in serum-free RPMI-1640 and exposed to AdVGFP at multiplicity of infection (MOI) ranging from 50 to 1,000 for 2 h at 37° C. After washing twice, the transduced DCs were re-suspended in fresh cytokine-supplemented medium and further cultured for 2 days. Subsequently, the expressions of GFP and DC phenotypes were assayed by FACSCalibur flow cytometry (Becton Dickinson, Franklin Lakes, N.J., USA). For phenotype analysis, AdVGFP-infected DCs were stained with phycoerythrin (PE)-conjugated HLA class I, HLA class 11, CD86, CD54, and CD83 (PharMingen, San Diego, Calif., USA). And to determine CEA expression, the AdVCEA-infected DCs were labeled with anti-CEA MAb (clone; T84.66A3.1A.1F2) and then a fluorescein isothiocyanate (FITC)-conjugated secondary goat anti-mouse IgG antibody (Cappel, Aurora, Ohio, USA).

Figure 2:
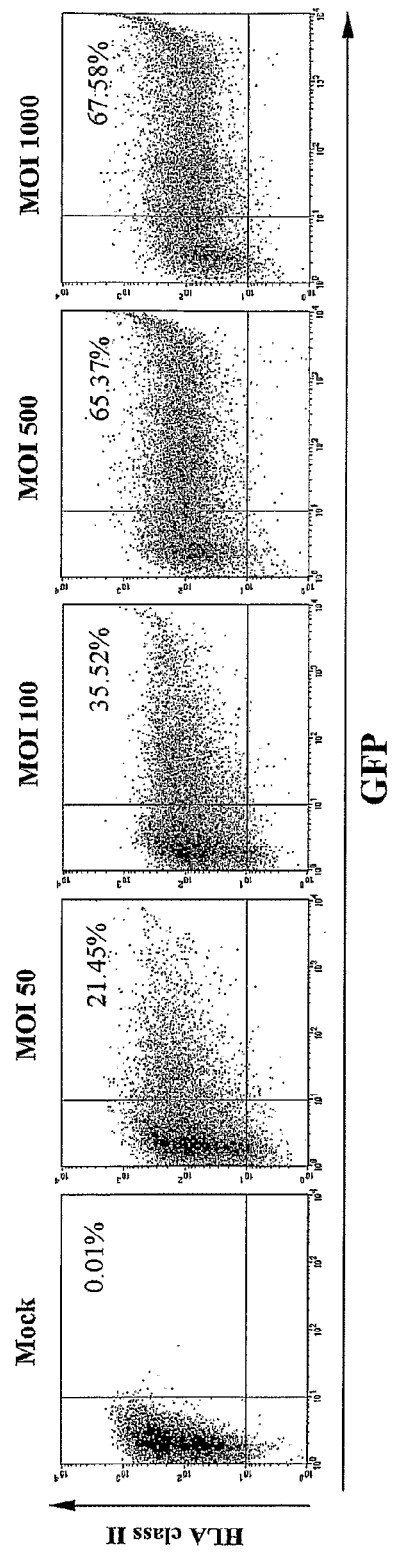

FIG. 1 shows transduction efficiency of adenovirus vector at various multiplicities of infection (MOI) and FIG. 2 shows surface marker expression of adenovirus-infected DCs. In FIGS. 1 and 2, isotype controls are shaded; light lines indicate mock-infected DCs; bold lines indicate AdVGFP-infected DCs. Also, all data are ungated for GFP-positive cells.

From the flow cytometry analysis performed to determine the transduction efficiency and the impact of AdV infection on the DC phenotypes, the monocyte-derived DCs proved amenable to the in vitro AdV-mediated gene transfer and its efficiency was increased in an MOI-dependent manner (FIG. 1). Also, AdV infection had no effect on the expression of MHC molecules (HLA classes I and II), while the AdV-infected DCs expressed slightly higher levels of CD86, CD54, and CD83 than the mock-infected DCs (FIG. 2). At MOI of 500, AdVGFP transduction rates ranged between 65 and 70% in DCs from three different donors.

Figure 3:
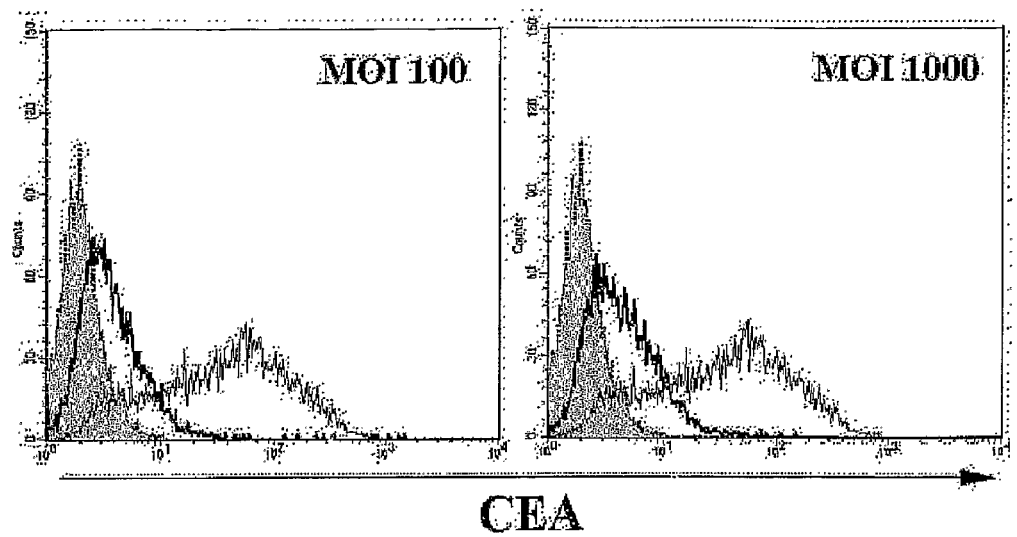
FIG. 3 shows surface expression of CEA that measured by flow cytometry.

Subsequently, the efficacy of CEA gene transfer into DCs with AdVCEA was evaluated. FIG. 3 shows surface expression of CEA in recombinant AdVCEA-infected DCs that measured by flow cytometry. In FIG. 3, isotype controls are shaded; light lines indicate CEA-positive colonic cancer cell line, LoVo; bold lines indicate AdVGFP-infected DCs. Even though DCs were transduced with AdVCEA within the range of MOI, the level of surface CEA was slightly increased and the dose (MOI) of AdVCEA had no effect on the surface expression of CEA (FIG. 3).

(2) Western Blot Analysis

For Western blot analysis, proteins in the cell extracts were separated using 8% sodium dodecyl sulfate-polyacrylamide gel electrophoresis (SDS-PAGE) and then transferred onto a nitrocellulose membrane. The membrane was incubated with 5% non-fat milk in PBS, and then with anti-CEA MAb for 2 h at room temperature. After washing, the membranes were incubated with an alkaline phosphatase-conjugated goat anti-mouse IgG antibody (Amersham Biosciences, Buckinghamshire, England) for 1 h at room temperature. Immunoreactive bands were detected using the ECL Western blotting analysis system (Amersham Biosciences, Buckinghamshire, England).

Figure 4:
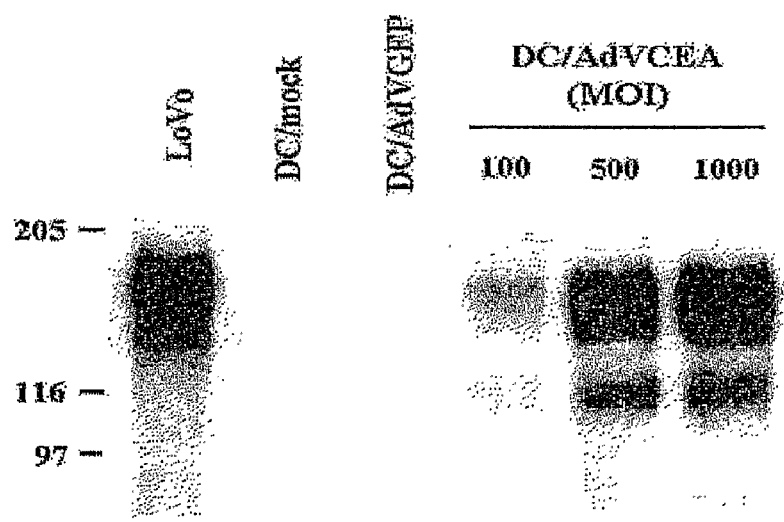
FIG. 4 shows the result of Western blot analysis of cells for the CEA expression and FIG. 5 shows immunofluorescent staining of DCs transduced with AdVCEA at MOI of 500.

FIG. 4 shows the result of Western blot analysis of cells for the CEA expression. LoVo cell extract was used as a CEA control for the Western blot analysis. Western blot analysis showed that the expression of CEA was increased in an MOI-dependent manner and, at an MOI of 500, the CEA level was similar with that of CEA-expressing colonic cancer cell line, LoVo (FIG. 4).

(3) Immune Fluorescence Microscopy

For immune fluorescence microscopy, the AdVCEA-infected DCs were attached to a slide by cytospin, and fixed for 10 min in 4% paraformaldehyde (Sigma). The slides were then washed with 0.2% Triton X-100 and anti-CEA MAb and negative control sera were added to each slide. After incubation for 30 min at 4° C. followed by a thorough washing in PBS three-times for 5 min, the slides were similarly treated with FITC-conjugated anti-mouse IgG. Subsequently, they were incubated for 5 min with 1 μq/ml of propidium iodide (Sigma), washed four times, mounted, and observed under a confocal laser scanning microscope (Bio-Rad, Hercules, Calif., USA) for the presence of nuclear and diffuse cytoplasmic fluorescence.

Figure 5:
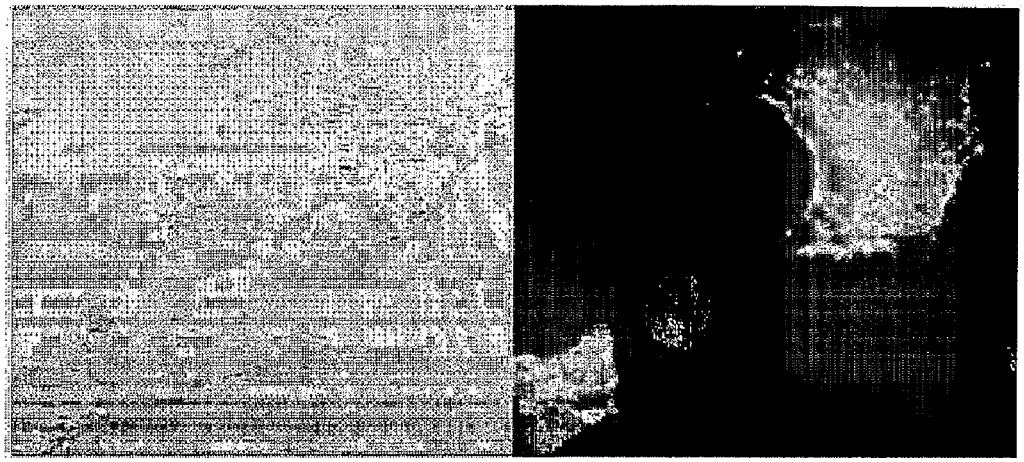

FIG. 5 shows immunofluorescent staining of DCs transduced with AdVCEA at an MOI of 500. Cells were cytospun to show the localization of CEA (Green) and of the nucleus (Red; 800×). Confocal microscopy revealed that CEA was mainly present in the cytoplasm of AdVCEA-infected DCs (FIG. 5)

Example 3

Estimation of Safety of AdV Vector by Apoptosis Detection

Whether AdV vector was safe to target cells or not was determined by apoptosis detection. For determining the apoptotic cell death, $5 \times 10^5$ DCs were exposed to AdVCEA at a MOI ranging from 100 to 1000 for 2 h. Subsequently, the cells were cultured for an additional 2 days in the presence of TNF-α and $PEG_2$. As control, mock-infected DCs were also incubated at a same condition. To induce apoptosis, mock-infected DCs were cultured in medium additionally containing 1 μg/ml of actinomycin D (AcD; Sigma). Staining and analysis of the apoptotic cells was performed with Annexin V-PE apoptosis detection kit (PharMingen), according to the manufacturer's instructions.

Figure 6:
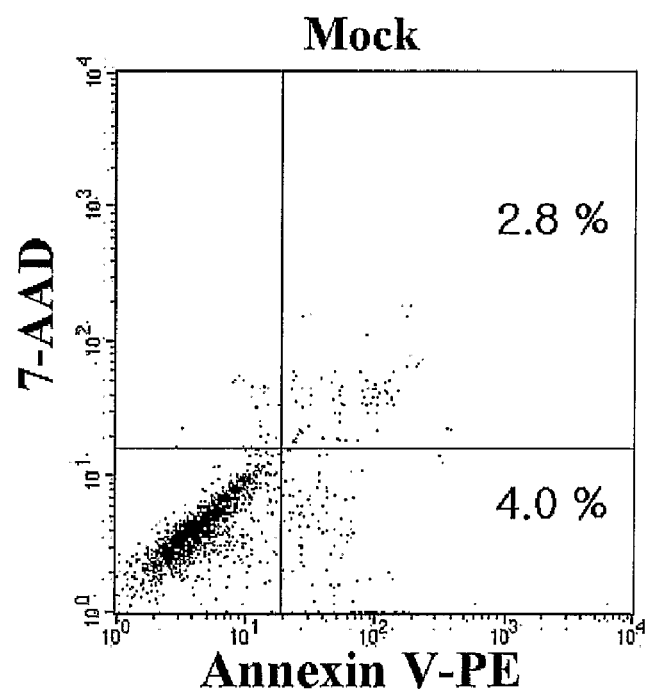
FIG. 6 shows the result of apoptotic analysis in mock-infected DCs.
Figure 7:
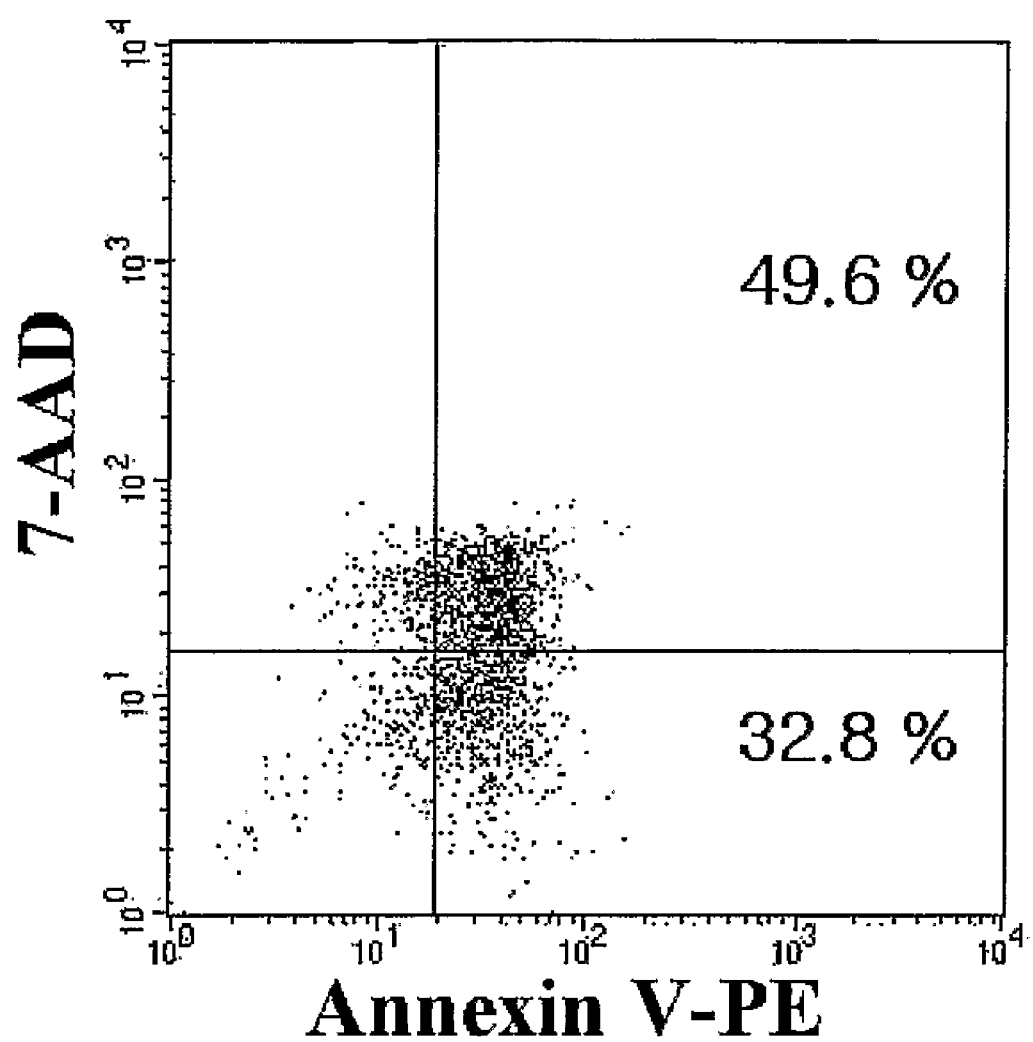
FIG. 7 shows the result of apoptotic analysis in mock-infected DCs cultured in medium additionally containing 1 μg/ml of actinomycin D.
Figure 8:
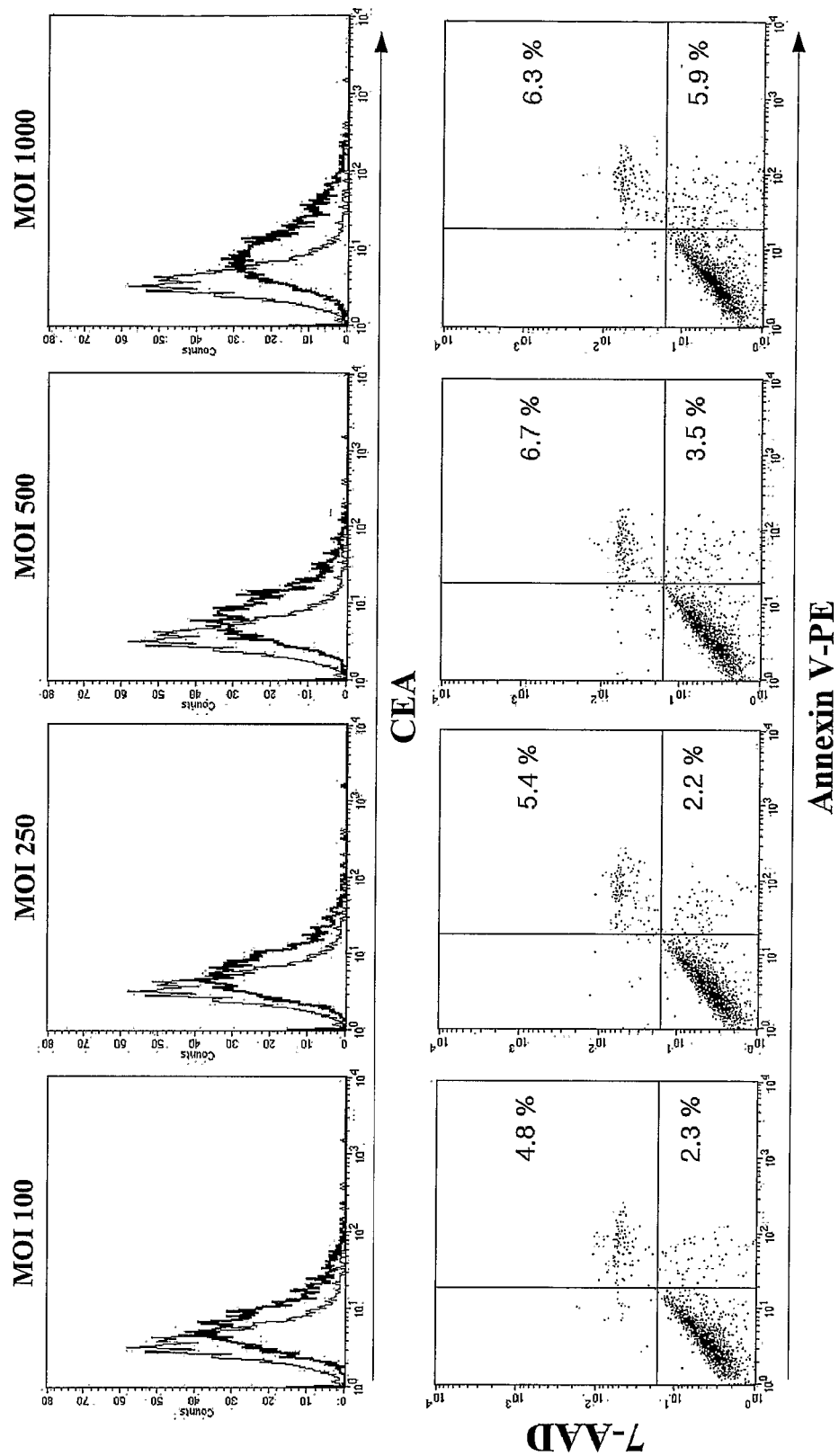
FIG. 8 shows surface expression of CEA (upper) and the result of apoptotic analysis in AdVCEA-infected DCs (lower).

FIG. 6 shows the result of apoptotic analysis in mock-infected DCs, and FIG. 7 shows the result of apoptotic analysis in mock-infected DCs cultured in medium additionally containing 1 μg/ml of actinomycin D. FIG. 8 shows surface expression of CEA (upper) and apoptotic analysis in AdV-CEA-infected DCs (lower). In FIGS. 6, 7 and 8, light lines indicate mock-infected DCs; bold lines indicate AdVGFP-infected DCs.

As shown from FIGS. 6, 7 and 8, even though the surface expression of CEA was increased in an MOI-dependent manner, the AdVCEA infection had no appreciable effect on apoptosis of DCs compared with that of mock-infected and AcD-treated DCs.

Example 4

Proliferation Assay by [$^3$H] Thymidine Incorporation Assays

Figure 9:
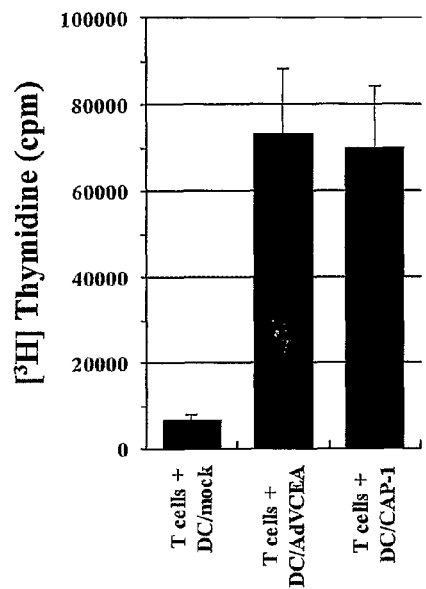
FIG. 9 shows the result of proliferation assay performed to determine the stimulatory capacity of AdVCEA-infected DCs.

The stimulatory capacity of the AdVCEA-infected DCs was investigated using standard [$^3$H] thymidine incorporation assays (FIG. 9).

Autologously matured DCs either transduced with AdV-CEA at an MOI of 500 or loaded with the CAP-1 peptide were co-cultured with the T-cell line, stimulated with CAP-1 peptide-loaded DCs for 2 weeks, at a responder:DCs ratio of 100:1 in quadruplets. After a 4-day incubation, [$^3$H]thymidine was added to each well (2 μCi per well), and after an additional 6 h incubation [$^3$H] thymidine uptake was measured using a liquid scintillation counter. Untreated DCs were used as negative controls. Means (±standard deviation, bars) were calculated from quadruplets. The degree of proliferation is indicated in counts per minute (cpm).

As shown from FIG. 9, HLA-A2-positive DCs, which transduced with AdVCEA, induced CEA-specific proliferative responses, whereas mock-infected DCs did not induce such a response.

Example 5

Generation of CEA-Specific T Lymphocytes and Cytolytic Activity Analysis by Chromium Release Assay Generation of CEA-Specific T Lymphocytes CEA-specific T-cell lines were generated in vitro by weekly stimulation of non-adherent peripheral blood lymphocytes from HLA-A2-positive healthy donors with irradiated autologous DCs either loaded with HLA-A2-restricted CAP-1 peptide or transduced with AdVCEA. The DCs were transduced with AdVCEA at a MOI of 500 and cultured for 2 days in fresh cytokine-supplemented medium containing 200 U/ml of TNF-α and 1 μg/ml of $PEG_2$. The CAP-1 peptide-loaded or AdVCEA-infected DCs were irradiated with 40 Gy that entirely prevented outgrowth in the control cultures, and the cells were seeded into 24-well plates at $5 \times 10^4$ cells per well. The non-adherent autologous peripheral blood lymphocytes were then added at $1.5 \times 10^6$ cells per well. After 7 days of co-culture with stimulators, the lymphocytes were harvested and resuspended at $5 \times 10^5$ per well. The T-cell lines were then restimulated with $1 \times 10^5$ cells per well of CEA-presenting, irradiated DCs. After 3 days, the cells were fed with 20 U/ml of interleukin-2 (Genzyme). The cells were harvested 4 days later, and then re-stimulated. On day 21, after harvesting the T-cell lines, their specificities were assayed.

Chromium Release Assay

After 3 weeks of stimulation with AdVCEA-infected DCs, the cultured T-cell lines were assayed for cytolytic activity using a 4 h chromium release assay. The effector cells were washed once, and re-suspended in RPMI containing 10% FBS. The CEA-expressing colonic cell lines used as targets were cultured in the presence of 100 U/ml of γ-interferon (γ-IFN; Genzyme) for 2 days to enhance the expression of MHC class I molecules. These peptide-loaded LCL and T2 cell lines were used for measurement of CEA-specific cytotoxic activity and K562 cells of natural killer (NK) cell activity. All target cells were then labeled with 100 μCi of $^{51}$Cr in 0.2 ml of RPMI containing 10% FBS at 37° C. for 1 h. After washing four times, the target cells were counted and seeded in triplicate in 96-well V-bottom plates at $5 \times 10^3$ per well. The effector cells were then added at the indicated effector-to-target (E/T) ratio. Following centrifugation at 1200 rpm for 2 min, the plates were incubated at 37° C. for 4 h. The supernatant fluids were then harvested and the $^{51}$Cr content was measured. The percent specific incorporation was calculated using the formula (cpm of experimental release minus cpm of spontaneous release) divided by (cpm of maximal release minus cpm of spontaneous release), multiplied by 100.

Figure 10:
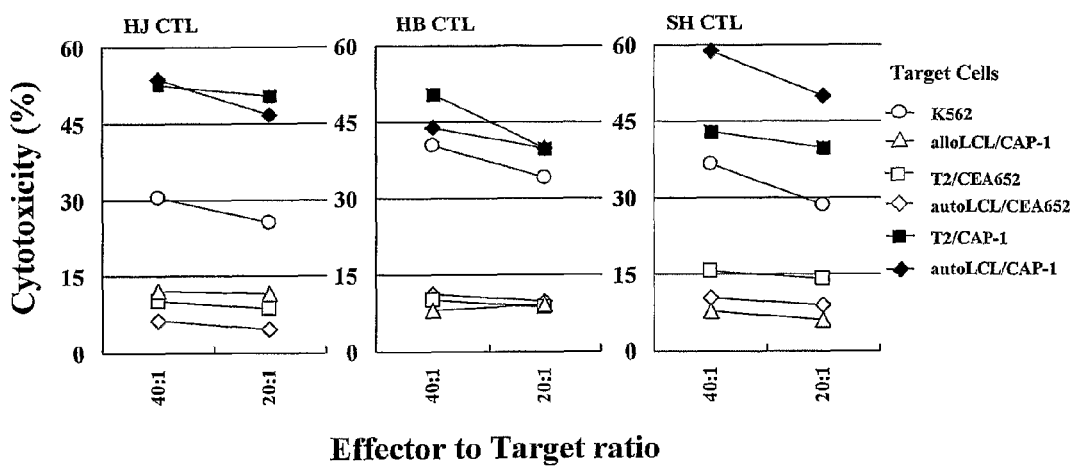
FIG. 10 shows cytotoxicity of T-cell lines growing in response to AdVCEA-infected DCs, which is determined by using K562, autologous (auto) or allogeneic (allo) lymphoblastoid cell line (LCL), and a HLA-A2-expressing T2 cell line as target cells.

FIG. 10 shows cytotoxicity of T-cell lines growing in response to AdVCEA-infected DCs. The target cells were K562, autologous(auto) or allogeneic(allo) lymphoblastoid cell lines(LCL), and a HLA-A2-expressing T2 cell line. The HLA-A2-restricted peptide YLSGANLNL (SEQ ID NO: 3), designated CAP-1, and the HLA-A24-restricted peptide TYACFVSNL (SEQ ID NO: 4), designated CEA652, were used for pulsing the target cells. CEA 652 peptide was used as a control. $^{51}$Cr-labeled target cells were incubated with effector cells to the indicated final effector: target ratios. The percentage lysis of target cells was measured in triplicate by using a standard $^{51}$Cr release assay. The T-cell lines were generated from donors of type; HJ(HLA type; A2; B7, 61), HB(HLA type:A2; B54, 15), and SH(HLA type: A2, 26, 844, 40).

As shown from FIG. 10, the cytotoxic activity of these T-cell lines was greater than 43% against CAP-1-pulsed autologous LCL and T2 target cell lines at a 40:1 E/T ratio. However, no CTL responses were observed against the CAP-1-pulsed allogeneic LCL or the CEA652 peptide-pulsed autologous LCL and T2 cell lines.

Figure 11:
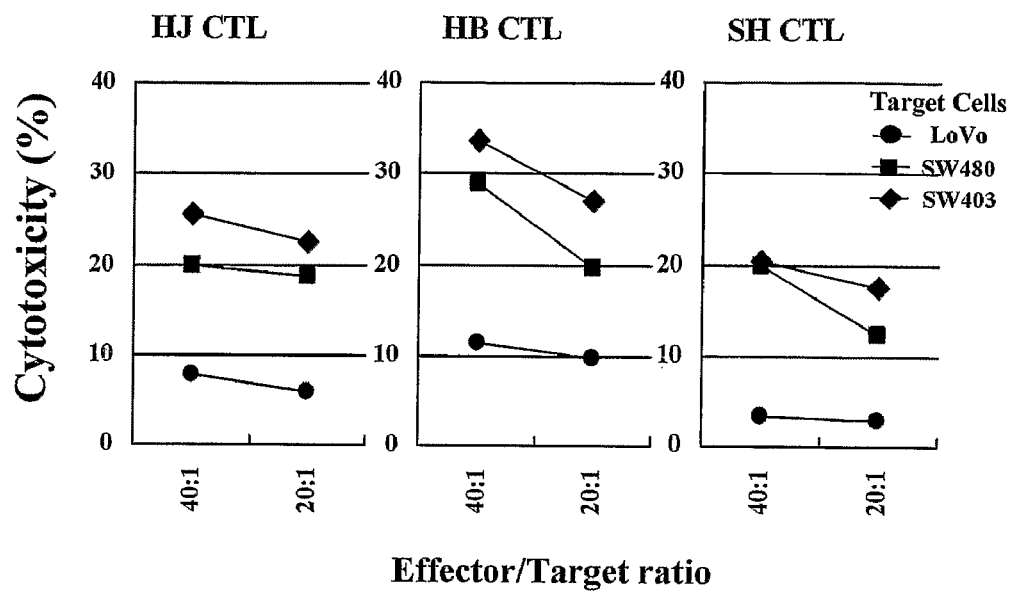
FIG. 11 shows cytotoxicity of T-cell lines growing in response to AdVCEA-infected DCs, which determined by using CEA-expressing colonic cancer cell lines, HLA-A2-negative (LoVo) or HLA-A2-positive (SW480 and SW403) as target cells.

FIG. 11 also shows cytotoxicity of T-cell lines growing in response to AdVCEA-infected DCs. CEA-expressing colonic cancer cell lines, HLA-A2-negative (LoVo) or HLA-A2-positive (SW480 and SW403), were used as target cells. The percentage lysis of target cells was determined in triplicate by using a standard $^{51}$Cr release assay. The T-cell lines were generated from donors of type; HJ (HLA type: A2; B7, 61), HB (HLA type: A2; B54, 15), and SH (HLA type: A2, 26; B44, 40).

As shown from FIG. 11, the T-cell lines specifically lysed the HLA-A2-positive carcinoma cells (greater than 20% at a 40:1 E/T ratio), while the HLA-A2-negative carcinoma cells were not lysed.

Example 6

Tumor Preventive Activity Test Using Animal Model

Female C57BL/6 mice (8 mice/group), 6 weeks age, were subcutaneously immunized 2 times at an interval of a week with $1\times10^6$ DCs infected with AdVCEA and AdVGFP at an MOI 500, $1\times10^6$ DCs reacted to CEA peptide, and $1\times10^6$ DCs alone (200 µl in PBS), respectively. Other groups were also subcutaneously inoculated 2 times with AdVCEA and AdVGFP at the same amount of MOI of 500 to determine the effect of recombinant virus alone, and a control group was inoculated with PBS 2 times. After one week, MC38/CEA2 tumor cells were injected at amount of $1\times10^6$ cells (200 µl in PBS) through the other side of hypoderm of the mice. The size of tumor was measured by Caliper. The mass of tumor was determined using the following equation. The major axis x the minor axis=mm². This experiment was performed two times and gave same results.

Figure 12:
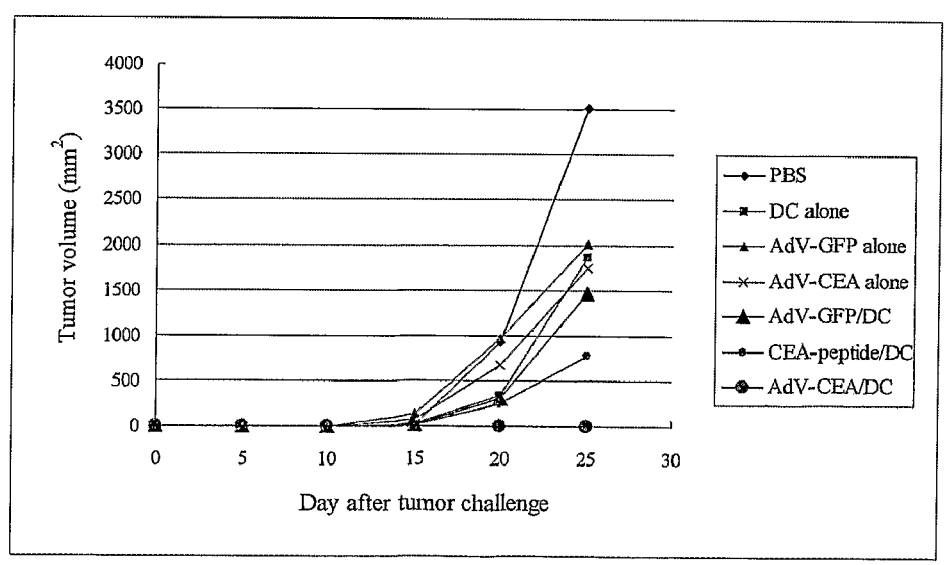
FIG. 12 shows the result of an experiment using animal models to determine the tumor preventing effect of AdVCEA-infected DCs according to the present invention.

As can be seen from FIG. 12, AdVCEA/DC prevented tumors in all 8 mice and the preventive effect was maintained for 12 weeks. CEA-peptide/DC and AdVGFP/DC could control tumors in 4 and 3 of the 8 mice, respectively. However, tumor was generated in all 8 mice in case of AdVCEA alone, AdVGFP alone and PBS.

Example 7

Tumor Therapeutic Activity Test Using Animal Model

C57BL/6 mice (10 mice/group) were subcutaneously inoculated with MC38/CEA2 cell line of $5\times10^5$, and then they were treated 2 times at an interval of a week when tumor mass of 3 mm in diameter was detected.

The test groups were AdVCEA/DC, AdVGFP/DC, CEA-peptide/DC, DC alone, AdVCEA alone, AdVGFP alone and so on, with PBS used for a control group. The survival rates were determined at an interval of a week. This experiment was performed two times and gave same results.

Figure 13:
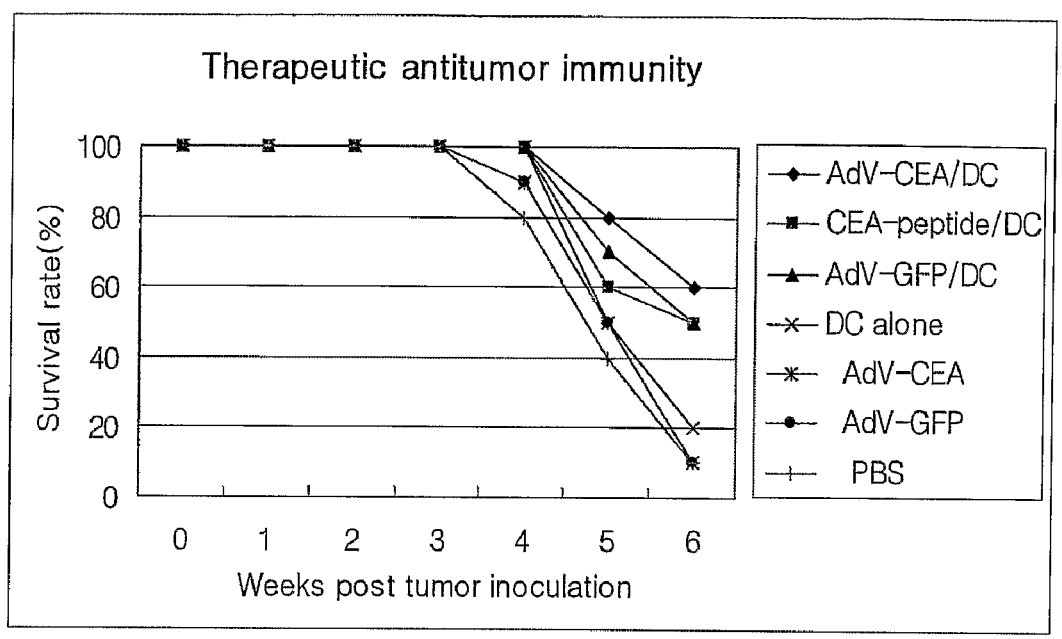
FIG. 13 shows the result of an experiment using animal models to determine the tumor treating effects of AdVCEA-infected DCs according to the present invention.

As can be seen from FIG. 13, AdVCEA/DC of the several test groups gave a result of the highest survival rate and the smallest mass of tumor. That is, AdVCEA/DC was more effective to control tumors than DC alone and recombinant adenovirus alone expressing CEA, a tumor antigen protein.

INDUSTRIAL APPLICABILITY

As described above, according to the present invention, vaccines and treating agent specific to several kinds of tumors, not limited to a kind of tumor, can be developed because the present invention use CEA as a tumor-related antigen and induce CEA-specific cytotoxic T lymphocytes.

Also, according to the present invention, the effect of treating tumors is excellent because using DCs as antigen-presenting cells in the present invention can induce both humoral and cell-mediated immune materials.

Especially, according to the present invention, CEA-specific cytotoxic T lymphocytes can be induced in vitro. Therefore, the method for in vitro induction can be used more effectively for tumor vaccine and cell-mediated immunotherapy than the method for in vivo induction.

Further, immunotherapy according to the present invention could function as a perfect therapy to give excellent treating effects and to prevent recurrent risk and metastasis of cancer when it is used with usual chemotherapy or radiotherapy as combined therapeutic method.

What is claimed is:

1. A recombinant adenovirus comprising a nucleic acid sequence encoding a carcinoembryonic antigen (AdVCEA) having Accession Number KCTC 10649BP.

2. An isolated AdVCEA-transduced dendritic cell which generates CEA-specific cytotoxic T lymphocytes, wherein the AdVCEA is a recombinant adenovirus comprising a nucleic acid sequence encoding a carcinoembryonic antigen according to claim 1.

3. An isolated AdVCEA-transduced dendritic cell which generates CEA-specific cytotoxic T lymphocytes, wherein the AdVCEA is a recombinant adenovirus comprising a nucleic acid sequence encoding a carcinoembryonic antigen according to claim 1, wherein said dendritic cell generates CEA-specific cytotoxic T lymphocytes in vitro.

4. A pharmaceutical composition for tumor treatment comprising the dendritic cell, wherein the dendritic cell is an AdVCEA-transduced dendritic cell which generates CEA-specific cytotoxic T lymphocytes, wherein the AdVCEA is a recombinant adenovirus comprising a nucleic acid sequence encoding a carcinoembryonic antigen according to claim 1.

5. A method for generating CEA-specific cytotoxic T lymphocytes in vitro, said method comprising:
   transducing a dendritic cell with the AdVCEA according to claim 1;
   incubating said transduced dendritic cell; and
   contacting the transduced dendritic cell with T lymphocytes.

6. The method according to claim 5, wherein said transducing step is performed at MOI of 100-2,000.

7. The method according to claim 6, wherein said transducing step is performed at MOI of 500-1,000.

8. A pharmaceutical composition for tumor treatment comprising a dendritic cell, wherein the dendritic cell is an AdVCEA-transduced dentritic cell which generates CEA-specific cytotoxic T lymphocytes, wherein the AdVCEA is a recombinant adenovirus comprising a nucleic acid sequence encoding a carcinoembryonic antigen according to claim 1, wherein said dendritic cell generates CEA-specific cytotoxic T lymphocytes in vitro.

* * * * *